United States Patent [19]

Beriozkina et al.

[11] Patent Number: 5,795,712
[45] Date of Patent: Aug. 18, 1998

[54] COMPOSITIONS FOR USE IN METHODS FOR NON-DESTRUCTIVE TESTING OF MATERIALS AND WARES

[75] Inventors: Nadejda G. Beriozkina; Ilia O. Leipunsky; Victor J. Maklashevsky, all of Moscow, Russian Federation

[73] Assignees: Marvic Ltd., Moscow, Russian Federation; Marotta Scientific Controls, Inc., Montville, N.J.

[21] Appl. No.: 752,547

[22] Filed: Nov. 20, 1996

Related U.S. Application Data

[62] Division of Ser. No. 329,203, Oct. 26, 1994.

[30] Foreign Application Priority Data

Jun. 6, 1994 [RU] Russian Federation ............ 94021094

[51] Int. Cl.$^6$ ...................................................... C09K 11/07
[52] U.S. Cl. ............................................. 436/5; 252/408.1
[58] Field of Search ................................... 422/56–58, 61, 422/83, 85; 436/5; 252/408.1

[56] References Cited

U.S. PATENT DOCUMENTS

| | | |
|---|---|---|
| 1,753,301 | 4/1930 | Pitschner . |
| 2,007,285 | 7/1935 | Schauffele et al. . |
| 2,310,111 | 2/1943 | Nordlander . |
| 3,464,796 | 9/1969 | Friedlander . |
| 3,830,094 | 8/1974 | Leger . |

FOREIGN PATENT DOCUMENTS

| | | |
|---|---|---|
| 667845 | 6/1979 | Russian Federation . |
| 832411 | 5/1981 | Russian Federation . |
| 1610349 | 11/1990 | Russian Federation . |
| 1661632 | 7/1991 | Russian Federation . |

*Primary Examiner*—Lyle A. Alexander
*Attorney, Agent, or Firm*—Hopgood, Calimafde, Kalil & Judlowe, L.L.P.

[57] ABSTRACT

A non-destructive testing method for revealing surface and through defects in materials and articles. The method comprises filling up defects with a volatile penetrant, applying indicator material to a surface to be tested, removing the indicator material from the surface and registrating defects according to the presence color spots, shapes and dimensions which are functions of shapes and dimensions of real defects. The indicator material comprises a gas-permeable base with applied sulfonephthalein indicator in the range of $10^{-4}$ to $10^{-3}$ grams per 1 cubic centimeter of the base.

5 Claims, 2 Drawing Sheets

COMPOSITIONS FOR USE IN METHODS FOR NON-DESTRUCTIVE TESTING OF MATERIALS AND WARES

RELATED APPLICATIONS

This is a divisional application of Ser. No. 08/329,203 filed Oct. 26, 1994.

BACKGROUND OF THE INVENTION

1. Field of the Invention

The invention relates to the testing technology, and more particularly relates to methods for non-destructive testing with the help of penetrating substances, and may be used for revealing through and blind surface defects in materials and wares as well as for evaluating their dimensions.

2. Description of the Prior Art

Non-destructive testing methods, using penetrating substances, are attractive due to their simplicity and graphicity.

For revealing blind surface defects dye capillary methods are usually used, which methods comprise applying at the tested surface a coloured penetrant, typically this is a red paint, then removing an excess of the penetrant from this surface and applying at this surface a developer, typically this is a thin layer of white paint, which extracts the penetrant from defects and makes them "visible."

For revealing through defects leak detection methods are usually used, which methods use any test gas or liquid substance, filling up tested article under high pressure.

The method for detecting through and blind surface defects during tightness and strength testing is developed in Russia (Soviet Union No. 832411, published May 28, 1981), which method includes filling a pressure vessel with the indicator fluid, building up a pressure, holding this vessel for 30–120 minutes, applying an indicator paste at the external surface of this vessel and revealing through defects, and hereupon removing the indicator fluid from this vessel and from its internal surface, applying the indicator paste on this internal surface and revealing surface defects. But this method was designed for the limited set of test objects, namely for the closed vessels, made of strong materials. Moreover, this method has low sensitivity, especially in revealing through defects, which in turn depends on the thickness of the vessel wall, on the pressure inside of tested vessel, and on the viscosity of the indicator fluid.

Some years ago the new capillary-diffusion method for non-destructive testing of composite materials is developed in Russia (Proceedings of Moscow International on Composite Conference, November 14–16, pp. 773–777), which allows to reveal through and blind surface cracks, pores, porous zones and to evaluate sizes of defects. The excess of a penetrant evaporates from the tested surface, whereupon the penetrant begins to evaporate out of the defects. One puts on the tested surface the indicator coverings, which change their color when absorbing penetrant vapors. Color spots at the indicator coverings point to the presence of through or/and blind surface defects in the tested ware. However, this method does not allow to reveal defects having a depth less than 0.3 mm and a width less than 1 micrometer, which restricts the set of tested objects to a great extent and limits the sensitivity of testing.

For applying a penetrant at the tested surface one usually use a brush or an apparatus, which includes a reservoir for a penetrant and a sprayer, for example, aerosol bulb HELLING, for applying a liquid penetrant in form of small drops, spreading on the surface and forming a continuous layer of a liquid penetrant at the surface of tested object. Such apparatus does not contain a chamber for a specimen and does not allow applying a penetrant by means of adsorption and/or capillary condensation of penetrant vapours from the gas phase, which results in decreasing the sensitivity of testing and in limiting the variety of tested wares.

The capillary testing method was developed in Russia, which used the apparatus for applying the penetrant from gas phase, which contains the sealed sample chamber with a blow-off valve, the joined reservoir for the penetrant fitted with a heater and a differential manometer, and a vapor collector joined to the valve (Soviet Union No. 1661632, published Jul. 7, 1991). The described known apparatus is designed for filling defects with vapors. This known apparatus allows to fill only empty defects of the width less than 80 micrometers, but it does not allow to fill defects, which contain the condensed atmospheric moisture, as well as defects of the width more than 80 micrometers.

For making defects "visible" during testing by means of penetrating substances various types of indicator materials are used. For example, in dye capillary method the developer in the form of white paint is usually used, which paint is removed from the tested surface with special solvents, when testing is finished. This procedure demolishes traces of reveals defects.

Another type of indicator materials is the indicator covering, i.e. the material, comprising a base and a sensitive component, applied on this base, which keeps traces of revealed defects being removed as a unit from the tested surface.

There is the indicator material, developed in Russia, which comprises the base, made of fabric or filter paper, and the sensitive component, consisted of bisodium fluorescine salt (Soviet Union No. 667845, published Jun. 25, 1979). This indicator material is designed for registration weld defects by means of storing up moisture, penetrating through defects, followed by ultraviolet illumination, which initiates luminescence of wet spots. The above indicator material does not allow to reveal capillary defects, containing ammonia solutions, because of its low sensitivity.

There is another indicator material, developed also in Russia, which comprises the base, made of a cotton fabric, and the sensitive component, consisted of copper sulphate (Soviet Union No. 1610349, published Nov. 30, 1990). However, the chemical reactions, which proceed in this material in the presence of ammonia and which cause the change of the material color from light green to light blue, do not provide the adequate contrast of color change, which in turn restricts the sensitivity of the material. Moreover, the net structure of the indicator material base restricts its resolving power and does not allow to discern any color spots of sizes less than the fabric base cell dimensions, which also restricts the resolving power of the material. Besides that, this known indicator material is designed for leakage testing of closed articles, into which compressed ammonia is carried, which restricts a range of tested wares to a considerable extent.

SUMMARY OF THE INVENTION

The above survey of methods and means of revealing through and blind surface defects with the help of penetrating substances indicates, that these methods are applicable to a very limited circle of tested articles and, besides that, have restrictions in the sensitivity. To a great extent the said restrictions are connected with both a manner of applying a penetrant and properties of a registering (indicator) material.

It is an object of this invention to develop a method of non-destructive testing of materials and wares, which would allow to extend the range of tested materials and wares and to increase the sensitivity of testing.

Further, an object of the present invention is to design an apparatus for applying the penetrant from gaseous phase, which also allows to extend the range of tested materials and ware and to increase the sensitivity of testing.

A still further object of the present invention is to develop an indicator material of high sensitivity.

An even further object of the present invention is to provide an indicator material of variable sensitivity, which would allow not only increase the circle of tested materials, but also to evaluate the amount of ammonia gas, absorbed by the said material.

According to the present invention the method for non-destructive testing of materials and wares comprises applying a volatile penetrant at their surfaces and filling up defects of any and all sizes by means of adsorption of penetrant vapours from the gas phase, and/or by means of capillary condensation of penetrant vapours from the gas phase, and/or by means of dissolution of penetrant vapours from the gas phase in atmospheric water condensate, which may occur inside the microcapillary defects, followed by registration of defects with he help of superimposable and removable indicator material, which absorbs penetrant vapours, flowing from defects, and changes its colour.

For realization of this method the apparatus, comprising a reservoir for a penetrant and a chamber for a sample, as well as the set of indicator materials, comprising gas-permeable base with applied indicator from sulfonephthalein group, are proposed.

DETAILED DESCRIPTION OF THE INVENTION

According to the present invention the method for non-destructive testing of materials and wares comprises applying a volatile penetrant at their surfaces by means of holding a tested specimen inside a closed chamber, filled with penetrant vapours, during a time interval, enough for adsorption of penetrant vapours at the surface of the specimen material, including defect wall surface, as well as for capillary condensation of penetrant vapours inside defects, and/or dissolution of penetrant vapours in condensed atmospheric water in microcapillary defects.

The method comprises also subsequent registration of defects by means of applying the indicator covering to the tested specimen surface for a time, enough for obtaining of images of defects in the form of color spots at the surface of the indicator covering with a geometry and a size of each color spot carrying information about the geometry and the size of the corresponding defect.

As the volatile penetrant the ammonia solution being used, applying penetrant being carried out from gas phase with the help of apparatus, containing the chamber for a sample and the reservoir for the penetrant, made in the form of closed vessel, fitted with two tubes of different length inside a vessel, the short tube being connected to the chamber for a sample.

In the capacity of the indicator covering the indicator material being used, which comprises the paper for chromatography/electrophoresis with applied indicator, belonging to the group of sulfonephthaleins, said indicator content being of $1 \times 10^{-4}$ to $1 \times 10^{-3}$ grams per 1 cubic centimeter of the said paper.

The ammonia content of solution is selected for test conditions within the range, for example, of 5–20 mass %.

Figure 1:
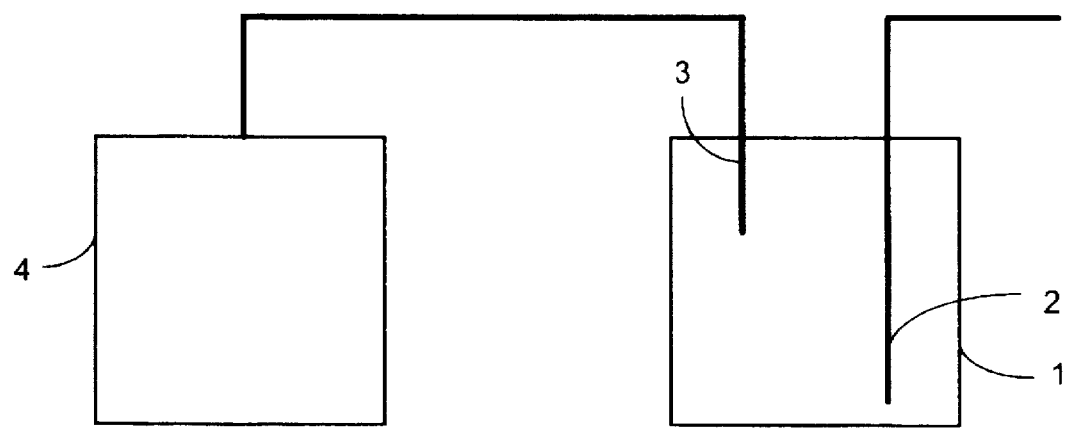
FIG. 1 is the schematic showing of apparatus for applying the penetrant from the gas phase.
Figure 2:
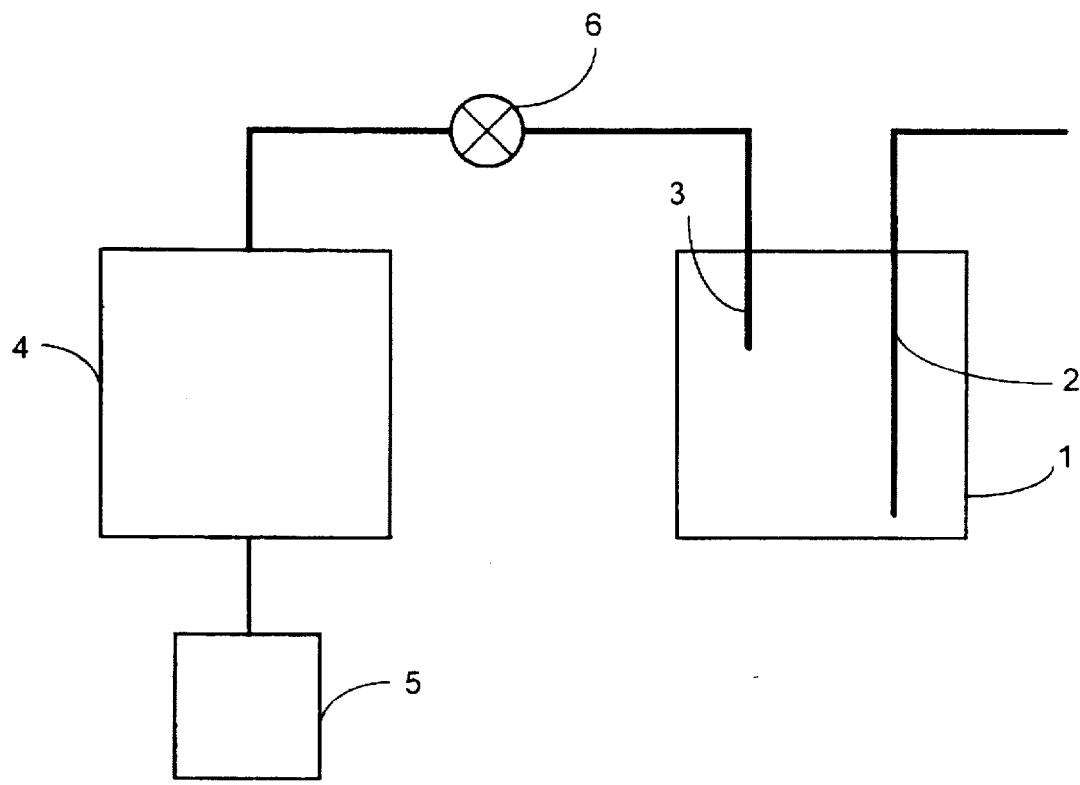
FIG. 2 is the schematic showing of apparatus for applying the penetrant from the gas phase, which additionally contains a forevacuum pump and a valve.

According to the present invention the apparatus for applying the penetrant from the gas phase, as it is shown in FIG. 1 and FIG. 2, comprises the reservoir 1 for the penetrant made in the form of the closed vessel with two tubes 2 and 3 of different lengths inside it, and the chamber 4 for a sample, the short tube 3 is joined to the chamber for a sample.

The long tube 2 is joined to air/gas supply, for example, to compressed air cylinder, or this tube may be extended to the atmosphere and thus joined to the air.

As it is shown in FIG. 2, the apparatus for applying the penetrant from the gas phase may be fitted with a forevacuum pump 5, joined to the chamber 4 for a sample, and with a valve 6, installed between the short tube 3 and the chamber 4 for a sample.

As the closed vessel a laboratory bubbler or, for example, a glass bottle or carboy, plagged with a stopper, said stopper having two holes for tubes of corresponding diameter, can be used.

As the chamber for a sample, for example, a laboratory exsiccator with a slip cover, a bell jar or a hood, can be used. Also, the chamber for a sample may be fabricated of polyethylene (plastic) film.

The apparatus for applying the penetrant from the gas phase may additionally be fitted with a manometer for measuring a pressure inside a chamber for a sample.

The apparatus for applying the penetrant from the gas phase, shown in FIG. 1, functions as follows.

The vessel for the penetrant 1 is filled with the penetrant, preferably ammonia solution, in such amount that the end of the long tube 2 being immersed in the liquid, but the end of the short tube 3 being above the level of the liquid inside the vessel. The external end of the short tube 3 is joined to the chamber for a sample 4, a test item being placed inside the said chamber. The external end of the long tube 2 is joined to pneumatic pump or a gas/air bottle. Gas/air is carried by tube 2 and passed through the layer of the penetrant inside the vessel 1. Thus the air inside the vessel is saturated with ammonia solution vapors, the gas pressure inside the vessel is increased, and the air, saturated with ammonia solution vapors, is conveyed by the tube 3 inside the chamber 4 with the test item. The test item is held in the chamber 4 for a given time interval.

Penetrant vapors, i.e. molecules of solvent and ammonia, are adsorbed at the surfaces of the test item, including the surfaces of defects. In this time two processes, namely, the capillary condensation of solvent vapors and dissolution (chemosorption) of ammonia in the condensate, concurrently take place inside the microcapillary defects.

If the material of the tested item has high wettability, the chance is, that the microdefects in this material are filled up (at least partially) with atmospheric wet condensate. In this case it is impossible, using traditional techniques, to fill up such defects by means of applying any liquid penetrant on the tested surface without any preliminary procedure. But the declared apparatus allows to make ammonia solution in such defects by means of dissolving (chemosorbing) of ammonia gas in the said condensate. In other words, the declared apparatus allows to apply the penetrant on the surface of tested ware from the gas phase and partially or completely fill up defects, exiting onto the surface.

The apparatus for applying the penetrant from the gas phase, shown in FIG. 2, operates as follows.

The vessel 1 is filled with the penetrant, preferably ammonia solution, in such amount that the end of the long tube 2 being immersed in the penetrant, but the end of the short tube 3 being above the level of the penetrant in the vessel 1. The external end of the long tube 2 remains open, and the external end of the short tube 3 is joined to the chamber 4 through the valve 6. The forevacuum pump 5 is joined to the chamber 4. Inside the chamber 4 a tested item is placed. The valve is set in the closed position. With the help of the forevacuum pump 5 the air is evacuated from the chamber 4 within a certain time, enough for creating the forevacuum in the chamber 4. Then the valve 6 is set in the open position, whereby the pressure difference between the ends of the tube 3 is created, and filling up the chamber 4 with penetrant vapours from the vessel 1 is provided. At the same time, because of pressure difference between inside and outside the apparatus, the atmospheric air enters through the tube 2 and through the layer of the penetrant inward the vessel 1. In consequence the air inside the vessel 1 is additionally saturated with the penetrant vapours, the pressure of the gas atmosphere inside the vessel 1 is raised, and the air, saturated with penetrant vapours, is carried by the tube 3 into the chamber 4. Air flowing through the tube 2 is stopped, when the pressure inside and outside the apparatus is equalized. The tested item is held in the chamber 4 within a time, enough for condensing the penetrant in capillary defects and/or for its adsorption at surfaces of tested item material, including walls of defects, exiting onto the tested item surface.

Such apparatus allows to clear cavities of defects from condensed wet and/or from adsorbed layers of foreign agents before filling up defects with the penetrant. Whereby the declared apparatus extend the range of tested wares and increases the sensitivity of the test.

In accordance with the present invention, the indicator material contains a gas-permeable hydrophilic uniformly porous base, preferably, the paper for chromatography and/or electrolphoresis, which carries a chemical indicator belonging to the group of sulfonephthaleins, preferably, tetrabrom-m-cresolsulfonephthalein, dibrom-o-cresolsulfonephthalein, tetrabromphenolsulfonephthalein, and o-cresol-sulfonephthalein.

The indicator material is fabricated by impregnating the paper for chromatography/electrophoresis with indicator solution containing 0.01–0.1% of its mass of one of the said above indicators, followed by drying this paper until hydroscopic (equilibrium) moisture. The finished material carries the indicator ranging from $1 \times 10^{-4}$ to $1 \times 10^{-3}$ grams of dry substance per 1 cubic centimeter.

The indicator, existing in the finished indicator material, is partially dissociated into ions. The initial color of the indicator material corresponds to the color of the integral (not dissociated) form of the indicator. Entering ammonia into the indicator material accents ion equilibrium to the side of increasing concentration of dissociated form of the indicator, which causes the change in color of the indicator material.

The above said content of indicator in the finished indicator material is responsible for the initial "acid color" of the material as well as for its high sensitivity to ammonia. Increasing or decreasing the above said contents of the indicator results in degradation of the material sensitivity.

The indicator material may additionally contain a regulator of pH, for example, chorhydric acid in content of $1 \times 10^{-5}$ to $2 \times 10^{-5}$ grams per cubic centimeter of the paper. These specific contents of the regulator of pH provide a high color change contrast of indicator material and increase the sensitivity of testing.

The content of chlorhydric acid being less, it does not act as pH regulator, but the content of said acid being more, it does not provide high sensitivity of the material.

As it is pointed above, the indicator belonging to the group of sulfonephthaleins, used in the declared indicator material, is, preferably, tetrabrom-m-cresolsulfonephthalein, or dibrom-o-cresolsulfonephthalein, or tetrabromphenolsulfonephthalein, or o-cresolsulfonephthalein, in the case of the last the indicator material may additionally contain chlorhydric acid in content of $1 \times 10^{-4}$ to $1 \times 10^{-3}$ grams per 1 cubic centimeter of the paper.

Introducing the chlorhydric acid into the indicator material, containing o-cresolsulfonephthalein, said acid being in content of $1 \times 10^{-4}$ to $1 \times 10^{-3}$ grams per cubic centimeter of the paper, allows to extend the range of the tested wares, for example, at the expense of high-porous material items, and additionally makes it possible to use color tints of the indicator material for evaluating the amount of ammonia gas, absorbed by this material.

The detection of defects with the help of declared indicator material is carried out by means of superimposing it at the tested surface. Ammonia gas, emerging from defects, enters into the indicator material and changes its color.

The gas-permeable hydrophilic uniformly porous base, preferably, the paper for chromatography/electrophoresis, makes provision for diffusing the ammonia gas as in the liquid, so in the gas phase inside the indicator material. In turn, the ammonia diffusion inside the indicator material is responsible for enlarging the color change areas up to sizes, discernible by eye and larger, as time goes on.

If the defect is a single pore, the diffusion front in the indicator material has semispheroidal (or spherical segment) shape, and at the surface of the indicator material the round spot of another color appears against this defect, the color spot being enlarged mirror image of the pore orifice.

If the defect is a crack, the indicator material changes its color inside the semicylindroidal area, and the image of this crack is the line at-the surface of the indicator material.

If the defect is the pileup of many separate pores, which are in close proximity to each other, their images may merge together, as a result the color spot appears at the surface of the indicator material, the configuration of this spot corresponding to the configuration of the porous area of the tested surface.

Due to ammonia diffusion in the indicator material the depth of the area of color changing may run into thickness of the base in the course of the time. In this case images of defects appear at the external surface of the indicator material, and ammonia diffusion is going on further from the colored area of the indicator material into the atmosphere.

The evaluation of defect sizes with the help of the declared material is realized by means of superimposing this material at the tested surface with the preset stand time after applying the penetrant (ammonia solution), recording images of defects within the preset exposure time and examining obtained images of defects. Thereat, to estimate a width of a crack, or a diameter of a pore, it is sufficiently to fulfil only single recording images of defects, but to estimate depths of defects, recording images of defects should be repeated many times in the given stand time intervals. For examining images of defects the sizes of this images and their color tints are used.

EXAMPLE 1

In the capacity of test specimen the Sherwin PSM-5 (Ser. No. 12376) is used, said panel is made of Ni-Cr plated stainless steel plate and has five crack centres. The test specimen is placed inside polyethylene pack.

For applying the ammonia solution from the gas phase the apparatus is used, which is schematically shown in FIG. 1. In the capacity of the reservoir for the penetrant the glass bottle of volume 2 litres is used. About 1 litre of 10% ammonia solution is poured into this bottle, and this bottle is plugged by a cork with two holes of 1 centimeter diameter. Two silicon tubes of 1 centimeter external diameter are fed through the said holes, the end of one tube being immersed into the ammonia solution to the whole depth, and the end of the second tube being placed about 4–5 centimeters above the solution level inside the bottle. The external end of the tube, immersed into ammonia solution, is joined to the rubber hand pump. The external end of the second tube is set into the aforesaid polyethylene pack with the test specimen. Edging of the pack is pressed to this tube and fixed by a rubber ring.

With the help of the rubber hand pump one blows the air through the layer of ammonia solution, watching the inflation of the pack. The inflated pack with the test specimen is held within 5 minutes, then this pack is unfixed from the tube end, and the test specimen is removed.

For recording images of defects the indicator material is used, which is made of the chromatographic and electrophoresis paper, which contains tetrabrom-m-cresolsulfonephthalein, in content of $10^{-4}$ grams per 1 cubic centimeter of the paper.

Figure 3:
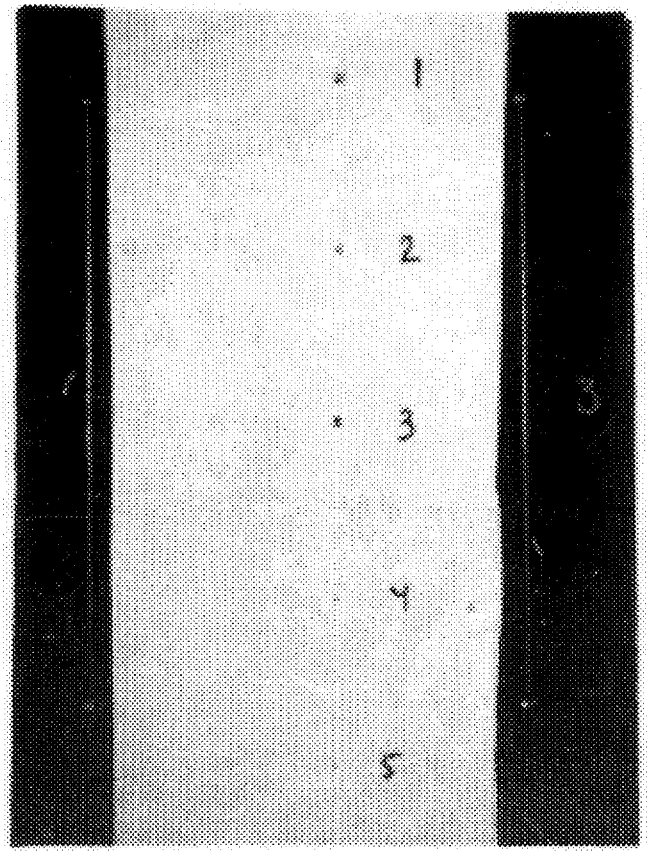
FIG. 3 is the indicator picture of Sherwin PSM-5 panel (Ser. No. 12276), obtained on the indicator material.

A strip of the indicator material is applied at the specimen surface and held within 1 minute, then it is removed from the specimen surface and one can see images of the above-said crack centres in the form of contract dark blue spots at the yellow background of the said paper. FIG. 3 shows a photograph (copy) of obtained images of the defects. By the form of the images it may be determined, that the defects 1, 2 and 3 are crack, emerging from the points (centres) in different directions, the defect 4 is a single crack (scratch) at the surface of the specimen, and the defect 5 is a dent less than 0.3 millimeters deep.

EXAMPLE 2

In the capacity of the sample a turbine blade of aircraft engine is used. The length of the blade is about 6 centimeters. The blade is placed into the chamber for a specimen, which is a laboratory exsiccator of volume about 1.5 litres.

For applying ammonia solution from the gas phase the apparatus is used, which principle scheme is shown in FIG. 2. In the capacity of the reservoir for the penetrant with two tubes a glass laboratory bubbler of volume about 0.5 litres is used. In the capacity of the short tube a glass outlet tube in the top of the bubbler is used. This outlet tube is connected with a silicon tube, which is connected by another end with a valve, installed in the cover of the exsiccator. In the capacity of a valve a three-way valve is used. The bubbler is filled with 15% ammonia solution up to half volume. The lower end of the long tube of the bubbler is immersed into solution, and the upper end of this tube is remained open in the environment. The fore-vacuum pump is joined to free end of the said three-way valve with the help of a rubber tube.

With the help of the three-way valve the exsiccator space is shut off from the bubbler and connected to the pump. Air is evacuated from the exsiccator within 5 minutes. By means of the three-way valve the exsiccator space is shut off from the pump and connected to the bubbler, whereby air saturated with water vapours and ammonia flows from the bubbler to the exsiccator. therewith, due to the difference in the air pressure between inside and outside the bubbler the air enters in the bubbler by the long tube and when passing through the ammonia solution layer additionally enriches the gas atmosphere inside the bubbler with water vapors and ammonia. The sample is held in the exsiccator, filled with water vapors and ammonia in the gas phase, within 15 minutes, then the exsiccator is opened and the sample is removed.

For recording the images of defects the indicator material is used, which is the chromatographic paper, which contains dibrom-o-cresolsulfonephthalein in content of $5\times10^{-4}$ grams per 1 cubic centimeter of the paper and chlorhydric acid in content of $1\times10^{-5}$ grams per 1 cubic centimeter of the paper.

A strip of the indicator material is applied at the convex surface of the blade and held within 30 seconds, watch being made on appearance of blue spots at the external surface of the material. The appearance and locations of these spots point to the presence of defects at the convex surface of the blade, which the form of branched cracks, initiated in the single point at the rear edge of the blade.

EXAMPLE 3

In the capacity of the sample the turbine blade after testing of its convex surface (see Example 2) is used.

For recording the images of defects the indicator material is used, which is the chromatographic and electrophoresis paper, containing tetrabrom-m-cresolsulfonephthalein in content of $5\times10^{-4}$ grams per 1 cubic centimeter of the paper and chlorhydric acid in content of $1.5\times10^{-5}$ grams per 1 cubic centimeter of the paper.

A strip of the indicator material is applied at the concave surface of the blade and held within 1 minute, watch being made on appearance of blue spots at the external surface of the paper. Relying on their shapes and their locations, the presence of defects at the concave surface of the blade is established, which are branched cracks, initiated in the single point at the rear edge of the blade.

EXAMPLE 4

In the capacity of the sample the turbine blade after testing its convex and concave surfaces (see Examples 2 and 3) is used.

For recording the images of defects the indicator material is used, which is the electrophoresis paper, containing tetrabromphenolsulfonephthalein in content of $1\times10^{-3}$ grams per 1 cubic centimeter of the paper and chlorhydric acid in content of $2\times10^{-5}$ grams per 1 cubic centimeter of the paper.

A strip of the said paper is folded and applied at both surfaces of the blade, the sharp (rear) edge of the blade being matched to the folding line, the said paper is held at the surfaces of the blade within 30 seconds and then is removed. The strip of the said paper is unfolded, and the images (micro symmetric about the folding line of defects revealed in the Examples 2 and 3 are viewed. Relying on their forms and their locations relative to each other, it is established, that these defects are through branched cracks, initiated in the single point at the sharp edge of the blade.

EXAMPLE 5

A sample is the ceramical ring of 4 centimeters diameter, 3 centimeters height and 2 millimeters thickness.

For applying the ammonia solution from the gas phase the apparatus described in the Example 1 is used. The sample is held inside the polyethylene pack, filled with water vapours and ammonia in the gas phase within 2 minutes, after that it is removed and held in the air within 1 minute.

In the capacity of the indicator material the paper for chromatography and electrophoresis, which contains dibrom-o-cresolsulfonephthalein in content of $1\times10^{-3}$ grams per cubic centimeter, is used.

A strip of the said paper is applied at the external surface of the sample and held within 30 seconds, after that the said paper is removed and the images of cracks are viewed in the form of contract blue lines at the yellow background of the paper.

EXAMPLE 6

A sample is the turbine blade with the ceramic coating. The length of the working part of the blade is about 6 centimeters, the thickness of ceramic coating is about 0.2 millimeters.

For applying the ammonia solution from the gas phase the apparatus described in the Example 1, is used. The sample is held in the polyethylene pack filled with water vapours and ammonia in the gas phase within 3 minutes, after that it is removed and held in the air within 15 minutes.

For recording the defects the indicator material is used, which is the chromatographic and electrophoresis paper, containing o-cresolsulfonephthalein in content of $1\times10^{-4}$ grams per 1 cubic centimeter of the paper and chlorhydric acid in content of $1\times10^{-4}$ grams per 1 cubic centimeter of the paper.

A strip of the said paper is applied at the surface of the sample and held within 15 seconds, then the said paper is removed from the surface of the sample, and the spots of various yellow color tints are viewed at its pink surface. Relaying on their color tints, shapes and sizes, it is established, that the ceramical coating has inhomogeneous porosity.

EXAMPLE 7

A sample is a part of porous composite material measured 4×7×0.8 centimeters with the protective coating of 0.5 millimeters thickness at one of the surfaces.

For applying the ammonia solution from the gas phase the apparatus, described in Example 1, is used, in which a polyethylene tubing of about 20 centimeters length and of about 30 centimeters perimeter is used as the chamber. One edge of the polyethylene tubing is fixed by a rubber ring to the short silicon tube, and another edge of the polyethylene tubing is fixed to the side surface of the sample by means of Scotch tape. At the surface of the part without protective coating is directed inward the polyethylene tubing. With the help of the rubber hand pump air is blown through the layer of ammonia solution until the inflation of polyethylene tubing, fixed by above manner. The inflated polyethylene tubing is held within 5 minutes, after that it is unfixed from the sample.

For recording through defects the indicator material is used, which is the paper for chromatography and electrophoresis, which contains o-cresolsulfonephthalein in content of $5\times10^{-4}$ grams per 1 cubic centimeter of the paper and chlorhydric acid in content of $5\times10^{-4}$ grams per 1 cubic centimeter of the paper.

A strip of the said paper is applied at the surface of the sample with the protective coating and held within 30 seconds, after that the said paper is removed from the sample surface and at the pink surface of the paper round spots of various tints of yellow color with diameters ranging from 0.5 to 3 millimeters are viewed. The presence of spots points to the presence of through defects in the tested sample with protective coating. Relaying on the shapes of the spots it is established that the defects are pores of various diameters.

EXAMPLE 8

A sample is the plastic rod of about 5.5 centimeters length and about 3 centimeters diameter.

For applying the ammonia solution from the gas phase the apparatus, described in Example 1, is used. The sample is held inside the polyethylene pack with water vapours and ammonia in the gas phase within 5 minutes.

For recording the defects the indicator material is used, which is the paper for electrophoresis, which contains o-cresolsulfonephthalein in content of $1\times10^{-3}$ grams per 1 cubic centimeter of the paper and chlorhydric acid in content of $1\times10^{-3}$ grams per 1 cubic centimeter of the paper.

A strip of the said paper is applied onto cylinder surface of the sample and held within 1.5 minutes. Then the said paper is removed from the sample surface and yellow streak of about 0.1 millimeters wide and about 3.5 centimeters length is viewed at pink background of the paper, which streak is the image of longitudinal crack at the cylindrical surface of the sample.

So, the above description and examples presented show, that the declared method for non-destructive testing of materials and wares, the declared apparatus for applying penetrant and the declared indicator material allow to extend the range of test materials and wares and to increase the sensitivity of testing.

The important feature of the declared indicator material is the ability to recover the original properties, which makes is reusable. A major advantage of the declared indicator material is that it may be used not only in the declared method, but it may find much use in various fields of industry for detection of ammonia gas.

While the present invention has been illustrated only with above examples, it is contemplated that there are many other versions which do not depart from the spirit and scope of this invention.

What is claimed is:

1. An indicator for detecting defects during nondestructive testing of a surface for imperfections comprising:

a gas permeable base material, such as a chromatographic and/or electrophoretic paper, that is impregnated with a sulfonephthalein indicator in the concentration of 0.0001–0.001 grams per cubic centimeter and chlorhydric acid in the concentration range of 0.00001–0.00002 grams per cubic centimeter.

2. The indicator material according to the claim 1, wherein said indicator is tetrabrom-m-cresolsulfonephthalein.

3. The indicator material according to the claim 1, wherein said indicator is dibrom-o-cresolsulfonephthalein.

4. The indicator material according to the claim 1, wherein said indicator is tetrabromophenolsulfonephthalein.

5. An indicator for detecting defects during nondestructive testing of a surface for imperfections comprising:

a gas permeable base material, such as a chromatographic and/or electrophoretic paper, that is impregnated with a o-cresolsulfonephthalein in the concentration of 0.0001–0.001 grams per cubic centimeter and chlorhydric acid in the concentration range of 0.0001–0.001 grams per cubic centimeter.

* * * * *